| United States Patent [19] | [11] Patent Number: 5,077,435 |
| Kimbrell et al. | [45] Date of Patent: Dec. 31, 1991 |

[54] PREPARATION OF HALOHYDROXYPROPYL-TRIALKYLAMMONIUM HALIDES

[75] Inventors: Russell B. Kimbrell, Angleton; Christian D. Kneupper, Lake Jackson; Ruben L. Krause, West Columbia, all of Tex.

[73] Assignee: The Dow Chemical Company, Midland, Mich.

[21] Appl. No.: 580,988

[22] Filed: Sep. 12, 1990

[51] Int. Cl.$^5$ .......................................... C07C 213/04
[52] U.S. Cl. .................................................. 564/292
[58] Field of Search .......................................... 564/292

[56] References Cited

U.S. PATENT DOCUMENTS

| 2,876,217 | 3/1959 | Paschall | 564/292 |
| 3,134,788 | 6/1964 | Noguchi et al. | 564/292 |
| 3,346,563 | 10/1967 | Shildneck et al. | 564/292 |
| 3,532,751 | 10/1970 | Langher et al. | 564/292 |
| 3,558,501 | 1/1971 | McGuire et al. | 564/292 |
| 4,450,295 | 5/1984 | van der Mass | 564/292 |
| 4,594,452 | 6/1986 | Reimschuessel et al. | 564/292 |
| 4,602,110 | 7/1986 | Tasset | 564/292 |

FOREIGN PATENT DOCUMENTS

| 61-134383 | 6/1986 | Japan | 564/292 |
| 2092150 | 8/1982 | United Kingdom | 564/292 |

*Primary Examiner*—James H. Reamer

[57] ABSTRACT

The present invention is a process for producing halohydroxypropyltrialkylammonium halides by reacting a trialkylamine salt with an epihalohydrin, the improvement comprising using 1,3-dihalo-2-propanol as a cosolvent. Using that cosolvent reduces the amount of diquaternary, dichloropropanol, and epoxy by-products formed. The cosolvent is preferably separated from the reaction mixture and recycled for use with additional trialkylamine salt and epihalohydrin. The process is particularly useful in preparing chlorohydroxypropyltrimethylammonium chloride.

14 Claims, No Drawings

PREPARATION OF HALOHYDROXYPROPYL-TRIALKYLAMMONIUM HALIDES

BACKGROUND OF THE INVENTION

This invention relates to the preparation of halohydroxypropyltrialkylammonium halides.

Halohydroxypropyltrialkylammonium halides are known to be useful as intermediates used in modification of natural and synthetic polymers, particularly in production of cationic polysaccharides, e.g. starch.

Halohydroxypropyltrialkylammonium halides are generally prepared by reaction of certain trialkylamines or their salts with epihalohydrins for instance by methods taught in European Patent Application No. 55,796 and U.S. Pat. Nos. 2,876,217: 3,135,788: 4,450,295 and 4,594,452. U.S. Pat. No. 2,876,217 discloses reactions of epihalohydrin and certain tertiary amines or salts in aqueous systems at a pH of at least about 5. Use of such a method results in a series of by-products, including unreacted epihalohydrins and 1,3-dihalo-2-propanol, which are preferably removed by careful purification by solvent extraction or vacuum distillation. European Patent Application No. 55,796 and U.S. Pat. No. 3,135,788 also disclose aqueous systems for similar reactions which require careful purification. U.S. Pat. No. 4,594,452 discloses the use of certain organic solvents which are solvents for epichlorohydrin and a trialkylammonium salt. U.S. Pat. No. 4,450,295 discloses certain combinations of aqueous and organic solvents for such reactions. These methods involve handling and removing a solvent material in addition to by-products. When the solvent is removed a solid product which readily deliquesces is produced. Generally, production of a solid product not only requires extra steps such as solvent removal and avoiding deliquescensce, but is also unnecessary because product halohydroxypropyltrialkylammonium halides are often sold commercially as aqueous solutions.

Alternatively, allyltrialkylammonium compounds are treated with such compounds as hypochlorous acid to form the corresponding chlorohydrins such as by the processes disclosed in U.S. Pat. Nos. 3,346,563: 3,532,751; and 3,558,501. Yield of by-products can be high as reported in U.S. Pat. No. 3,346,563, where about 30 percent by-product is noted.

Known methods of purifying chlorohydroxypropyltrialkylammonium chloride products include those taught in U.S. Pat. No. 2,876,217. These processes remove some by-products but frequently are ineffective in removing bis(trialkylammonium chloride)-2-hydroxypropanes (diquaternary compounds). Removal of diquaternary compounds generally requires processes such as fractional crystallization after solvent removal. Fractional crystallization is generally tedious and generally results in loss of product. Additional by-products which require careful separation include dihalopropanol (produced from epihalohydrin) and 2,3-epoxypropyltrialkylammonium chlorides (epoxy compounds).

Glycidyl quaternary ammonium salts have been prepared from the reaction of epihalohydrins with tertiary amines in the presence of a small quantity of 1,3-dihalohydrin as disclosed in Japanese Kokai 61-134383 (1986). Preferably, the dihalohydrin is present in an amount equivalent to 1-15 mole percent, more preferably 2-8 mole percent, relative to the tertiary amine. The purpose of the dihalohydrin is to reduce the amount of quaternary ammonium hydroxide by-product in the strongly alkaline solution containing the amine. The production of halohydroxypropyltrialkylammonium halides is generally preferred over the corresponding glycidyl compounds however, because the glycidyl compounds are relatively unstable and their purity can be greatly reduced during storage when compared to the halohydroxypropyltrialkylammonium halides.

It would be desirable to have a process of producing halohydroxypropyltrialkylammonium halides which avoids solids handling, has a simplified purification, and preferably, results in reduced production of dihalopropanol, epoxy and diquaternary by-products.

SUMMARY OF THE INVENTION

In one aspect the invention is in a method for producing halohydroxypropyltrialkylammonium halide by reacting, in a reaction mixture, a trialkylamine salt with an epihalohydrin, the improvement comprising using 1,3-dihalo-2-propanol as a cosolvent. Using such a cosolvent advantageously reduces the amount of diquaternary, dihalopropanol, and epoxy by-products formed. The process of the invention is particularly effective when the halogen is the same for all compounds in the reaction, e.g. producing chlorohydroxypropyltrialkylammonium chloride, using epichlorohydrin and 1,3-dichloro-2-propanol.

DETAILED DESCRIPTION OF THE INVENTION

Processes for preparing halohydroxypropyltrialkylammonium compounds from trialkyl amine salts and epihalohydrins are well known in the art. Exemplary of such processes are those taught in European Patent Application No. 55,796; U.S. Pat. Nos. 2,876,217: 3,135,788; 4,450,295 and 4,594,542 which patents are incorporated herein by reference in their entireties.

In the practice of the invention, any of these processes are used except that a 1,3-dihalo-2-propanol is used as a cosolvent with water. By cosolvent it is meant that the 1,3-dihalo-2-propanol and water dissolve both the epihalohydrin and the amine hydrohalide reactants. The 1,3-dihalo-2-propanol comprises at least about 10 weight percent of the reaction mixture which includes reactants and water. Preferably, the 1,3-dihalo-2-propanol comprises from about 30 to about 60, more preferably from about 50 to about 60 weight percent of the mixture. It is noted that as the amount of 1,3-dihalo-2-propanol is increased within these ranges, less diquaternary by-product is formed. Furthermore, when greater than about 50 percent 1,3-dihalo-2-propanol is present, an amount of epihalohydrin equimolar with the amine hydrohalide is miscible with the reaction mixture. There is preferably sufficient water present to dissolve the product halohydroxypropyltrialkylammonium halide. More preferably, there is sufficient water present to form a product aqueous solution which, after purification, contains from about 50 to about 65 weight percent, most preferably about 65 percent product halohydroxypropyltrialkylammonium halide: thus, the water most preferably comprises from about 30 to about 35 percent of the product solution.

Use of 1,3-dihalo-2-propanol is convenient because it is a solvent for both epihalohydrins and such trialkylamine salts as trimethylamine hydrochloride. As such it allows reaction of the reactants in a single phase. Use of a single phase increases the concentration of reactants in contact with each other: thereby increasing the reaction rate of the desired reaction. By-products are minimized, and smaller reactor volumes are suitable because of increased reaction rate. This cosolvent behavior is unexpected since 1,3-dihalo-2-propanol is not completely miscible with water and the addition of salts (in this case, the reactant and product ammonium halides) typically decrease the miscibility of organic compounds in water. Unexpectedly, the 1,3-dihalo-2-propanol increases the miscibility of all reactants and water.

The cosolvent is suitably mixed with the reactants by any method, for instance one or more of the reactants are suitably dissolved therein and, other reactant(s) added thereto. Preferably, the tertiary amine salt is in solution in water, and 1,3-dihalo-2-propanol is added to this solution to form an admixture. Then the epihalohydrin is added to the admixture, either over a period of time corresponding to the reaction time, or, if there is sufficient 1,3-dihalo-2-propanol to dissolve it, preferably all at once. Alternatively, the 1,3-dihalo-2-propanol is mixed with the epihalohydrin and added to an aqueous solution of the trialkylamine hydrohalide.

Advantageously, the cosolvent and reactants or solutions thereof, e.g. amine salt in water, are mixed together, either alone or in water, in equipment suitable for reaction and separation of product from reactants by means within the skill in the art such as using an agitated vessel, a kettle reactor or a flow reactor, plug or loop.

Conveniently, the process is carried out at atmospheric pressure. Any temperature at which the reaction proceeds is suitable, but in most instances, preferred temperatures range from about 0 to about 50° C., preferably from about 30 to about 50° C., more preferably from about 30 to about 40° C.

Among 1,3-dihalo-2-propanol cosolvents, the preferred cosolvents are those having both halogens the same, e.g. 1,3-dichloro-2-propanol or 1,3-dibromo-2-propanol, more preferred are those having the same halogen as the halogen desired in the halohydroxypropyltrialkylammonium salt, which will be the same as the halogen of the epihalohydrin source of the halogen in the product. Having all of the halogens on reactants and cosolvent the same, avoids products and by-products with mixed or different halogen species. It is, therefore, highly preferred that all halogen atoms in the reaction mixture be the same, e.g. that epibromohydrin and a trialkylamine hydrobromide be reacted in 1,3-dibromo-2-propanol to produce a bromohydroxypropyltrialkylammonium bromide: most preferably epichlorohydrin is reacted with a trialkylamine hydrochloride in 1,3-dichloro-2-propanol.

The process of the invention is especially suitable for the hydrohalides of trialkyl amines such as trimethylamine, tri-n-propylamine, dimethyl stearylamine, dimethyl dodecylamine, triethylamine, tri-n-propylamine, tri-n-butylamine, tri-n-hexylamine, dimethylmonoethylamine, dimethylmono-n-butylamine, dimethylcyclohexylamine, dimethyl-monoisopropylamine, methylethyl-n-propylamine, methylethyl-n-propylamine, methylethyl-n-butylamine, methyl dialkyl amines, and other tertiary amines having linear, branched, or cyclic hydrocarbon groups each independently containing from 1 to about 20 carbon atoms, preferably dimethyl stearyl amine, dimethyl dodecyl amine or trimethylamine, more preferably trimethylamine hydrohalides.

The salts of trialkyl amines are used rather than the free amines to avoid production of epoxypropyl (glycidyl) compounds rather than the desired halohydroxypropyl compounds. The salts are commercially available, or are formed in reactions within the skill in the art such as the reaction of the corresponding trialkylamine with an acid preferably a hydrohalic acid, more preferably the hydrohalic acid having the same halide as has the dihalopropanol, e.g. hydrochlorides when 1,3-dichloro-2-propanol is used.

Epichlorohydrin is the preferred epihalohydrin because it is readily available and chloride ion is considered more environmentally acceptable than other halides. Furthermore, epichlorohydrin forms 1,3-dichloro-2-propanol and, therefore, easily reaches an equilibrium with the preferred cosolvent.

After reaction of epihalohydrin and trialkylamine salt has reached a predetermined stage of completion, preferably is essentially complete, that is at least about 90 percent by weight, more preferably 99 percent of the limiting reactant (preferably the trialkylamine salt) is reacted, the 1,3-dihalo-2-propanol is separated from the product. Removal is suitably by any method within the skill in the art, but preferably by distillation, preferably azeotropic distillation, most preferably vacuum azeotropic distillation. These means of distillation are preferred because they provide economical separation and do not introduce foreign solvent material. Additionally, vacuum conditions minimize temperatures and resultant thermal degradation of product.

The azeotropic distillation preferably takes place in the presence of sufficient water to provide the azeotropic composition of water with the dihalopropanol, which is about 75 weight percent water. The azeotrope is heterogeneous: therefore, the water phase can be allowed to separate and reflux. Initially, there is advantageously enough water to allow loss due to solubility of water removed with the dihalopropanol (including dissolved water) and enough to provide water for the azeotrope. Because of the hetergeneous nature of the azeotrope which allows the water to reflux back, very little additional water will be needed.

Vacuum distillation can be accomplished at any pressure below atmospheric, conveniently from about 50 to about 100 mmHg corresponding to temperatures within the column varying from about 30° to about 90° C.

Preferably, the 1,3-dihalo-2-propanol, preferably with any unreacted epihalohydrin, is recycled. For instance, these compounds are advantageously removed from the aqueous solution of product by means within the skill in the art such as vacuum distillation or solvent extraction and returned to the reaction vessel for use in subsequent reactions. Most preferably the 1,3-dihalo-2-propanol is recycled until the 1,3-dihalo-2-propanol reaches a predetermined or, preferably, an equilibrium level.

When the concentration of 1,3-dihalo-2-propanol reaches the equilibrium level, substantially as much 1,3-dihalo-2-propanol reacts to produce epihalohydrin as is produced by the hydrohalogenation of epihalohydrin. At that point it is no longer advantageous to add or remove 1,3-dihalo-2-propanol.

Where removal by azeotropic distillation is insufficient to purify the product for a purpose, residual 1,3-dihalo-2-propanol can be removed by means within the skill in the art. Preferably, a solvent for 1,3-dihalo-2-propanol which separates from water, such as toluene, methylene chloride, chloroform, or carbon tetrachloride is used to remove residual 1,3-dihalo-2-propanol from the product. An extraction column is preferably used. An extraction column can have packing (such as Pall rings), perforated plates, agitated plates, or rotating contactors and sufficient stages to accomplish the degree of 1,3-dihalo-2-propanol removal that is desired, e.g. from a few stages to over twenty stages. Advantageously if the solvent (e.g. carbon tetrachloride) has greater density than the reaction product (e.g., aqueous chlorohydroxypropyltrimethylammonium chloride) the solvent is added at the head of the column and the column is operated such that the solvent is the continuous phase. The reaction product is admitted to the column at the bottom and flows upward through the column as the dispersed phase, finally being removed at the column top where it is allowed to coalesce into a separate phase.

Use of a 1,3-dihalo-2-propanol as cosolvent results in product halohydroxypropyltrialkylammonium halides having less diquaternary by-products, e.g. bis(trialkylammonium halide)-2-hydroxypropanes than would be present in the same product produced from the same starting materials and reaction conditions but using water or a organic solvent or cosolvent different from a 1,3-dihalo-2-propanol. Preferably, the product is produced substantially without diquaternary by-products. By substantially without it is meant that such by-products are present in amounts less than about 1 weight percent relative to the halohydroxypropyl-ammonium salt. More preferably, there is less than about 1 percent diquaternary by-product in an aqueous solution of about 65 weight percent product. It is believed that intermediates which would otherwise lead to diquaternary by-products are converted to halohydroxypropyltrialkylammonium halide, thus improving efficiency of use of raw materials.

Measuring such concentrations of diquaternary by-product is within the skill in the art, for instance, by liquid chromotography of an aqueous solution of halohydroxypropyltrialkylammonium halide product, which product is most preferably in a concentration of about 65 weight percent in water. Such liquid, preferably paired-ion chromatography is suitably conducted on a system such as the Waters Liquid Chromatograph System commercially available from Millipore, Waters, Chromatography Division. Such a system has a pump, sample injection system, radial column compression system, and a refractive index detector. Suitable columns include, for instance, C-18 reverse-phase columns. A paired-ion chromatograph reagent such as that prepared from about 3.98 g (grams) of 1-octane sulfonic acid, about 116 g sodium perchlorate, about 132 g methanol and about 1750 g high purity water filtered through e.g. 0.45 micron paper and degassed about 15 minutes under vacuum is suitably used as chromatographic solvent, and a solution such as about 5 percent methanol in water (similarly filtered and degassed) is suitably used to flush the column prior to periods of inactivity. These solution concentrations are optionally optimized for some liquid chromatography columns. Determining chromatograph parameters is within the skill in the art, but for the suggested system, suitable combinations include a pump flow rate of about 1.5 mL/min and using a detector having an internal temperature of about 40° C. The chromatograph system is preferably used with an integrator, such as that commercially available from Hewlett-Packard and designated as Model 3393. High purity standards are prepared by methods within the skill in the art and the system used to calibrate the system. The system is preferably purged with the paired-ion chromatography reagent at least until a flat baseline is obtained. Then a weighed sample is introduced into the system, e.g. using a syringe and sample injection valve. Peaks areas are obtained using the system and an integrator and compared with the calibration standard to ascertain concentration. This procedure is within the skill in the art and is taught, for instance, in Dow Analytical Method DOWM 100484 "1,2-Dihydroxypropyl Trimethylammonium Chloride and bis(Trimethylammonium Chloride)-2-Hydroxypropane in QUAT ™ 188 Cationic Monomer". QUAT 188 is a trademark of The Dow Chemical Company.

Furthermore, as measured by the same procedure, less 2,3-epoxypropyltrimethylammonium halide is produced as a by-product than is produced in the same reaction from the same starting materials and reaction conditions but using water or a organic solvent or cosolvent different from 1,3-dihalo-2-propanol. The concentration of epoxypropyl by-product is measured in the same paired-ion liquid chromatography procedure as is used for measuring the concentration.

Use of 1,3-dihalo-2-propanol as cosolvent also reduces loss of epihalohydrin to 1,3-dihalo-2-propanol because there is an equilibrium between it and the epihalohydrin which is pushed toward the epihalohydrin by the presence of excess 1,3-dihalo-2-propanol. Thus, use of epihalohydrin is more efficient than it would be where the only 1,3-dihalo-2-propanol is that produced from the epihalohydrin. For instance, typically, from about 10 to about 12 mole percent of epihalohydrin is lost to dihalopropanol when solvents other than 1,3-dihalo-2-propanol are used, but when at least an equilibrium amount of dihalopropanol is used as cosolvent, substantially no net loss of epihalohydrin to dihalopropanol is experienced.

The following examples are presented to illustrate the invention and are not to be interpreted as limiting it. All percentages, parts and ratios are by weight unless otherwise stated. Examples (Ex.) of the invention are designated numerically, while Comparative Samples (CS) are not examples of the invention and are designated alphabetically.

EXAMPLES

Examples 1–4 and Comparative Sample A: Preparation of 3-Chloro-2-hydroxypropyl Trimethylammonium Chloride in the Presence of Varying Amounts of 1,3-Dichloro-2-Propanol To a 100 ml round-bottomed flask continually agitated using a stirring bar and having a chilled water bath, is introduced an amount of an aqueous 58.77 weight percent solution of trimethylamine hydrochloride noted in Table 1. The temperature is held near isothermal at 30° C. by the small size of the reaction vessel and the water bath. Then an amount of reagent-grade 1,3-dichloro-2-propanol (DCP) noted in Table 1 is added. The temperature is allowed to equilibrate at 30° C. Then, with continuing agitation, an amount of epichlorohydrin equimolar in quantity to the trimethyl amine hydrochloride is added quickly using an addition funnel. An exothermic reaction is observed that gives rise to a temperature increase of a few degrees centigrade. In Examples 1–3, not all of the initial epichlorohydrin is soluble, and the agitated mixture appears cloudy until the epichlorohydrin has reacted or solubilized to the point that it no longer exists as a separate (dispersed) organic phase. A drop in reaction velocity is indicated by a rapid cooling in temperature and the chilled water bath is removed. This generally indicates a virtual completion of the reaction. Analysis using a Waters Liquid Chromatography System as described in the Specification verifies that the bulk of epichlorohydrin conversion is completed. Time intervals to achieve single-phase and to achieve reaction completion are noted in Table 1.

| Sample or Example Number | Reactant Quantities, grams | | | Time Intervals, until: (min.) | | Product Composition* in weight percent | | | |
|---|---|---|---|---|---|---|---|---|---|
| | TMA-HCl*** Aqueous | DCP† | Epi-chloro-hydrin | Single-Phase | Reaction Completion | Diol†† | Epoxide ††† | CHPTMAC* | DIQUAT ** |
| CS A* | 19.0 | 0 | 10.8 | 48.5 | 48.5 | trace | 2.53 | 65 | 2.23 |
| Ex. 1 | 19.0 | 15.0 | 10.8 | 19 | 35 | trace | .92 | 65 | 1.10 |
| Ex. 2 | 19.0 | 19.0 | 10.8 | 17 | — | .05 | 1.33 | 65 | 0.52 |
| Ex. 3 | 19.0 | 28.5 | 10.8 | 6.5 | 28 | .13 | 1.80 | 65 | <0.5 |
| Ex. 4 | 19.0 | 43.5 | 10.8 | 0 | 17 | — | — | 65 | <0.5 |

*normalized to 65 weight % CHPTMAC (3-chloro-2-hydroxypropyltrimethylammonium chloride) in water
**DIQUAT is 1,3-bis(trimethylammonium chloride)-2-hydroxypropane
***58.77 weight % aqueous solution of trimethylammonium hydrochloride (TMA-HCl)
†DCP is 1,3-dichloro-2-propanol
††Diol is 2,3-dihydroxypropyltrimethylammonium chloride
†††epoxide is 2,3-epoxypropyltrimethylammonium chloride
*Comparative Sample - not an example of the invention.
— indicates that no measurement is taken.

The data in Table 1 show that the diquaternary by-product (DIQUAT) is significantly reduced as the DCP cosolvent content is increased. Distillation of 1,3-dichloro-2-propanol from a sample product is illustrated by the following:

A 40-tray vacuum-jacketed glass column with sieve plates commercially available from Fisher Scientific, Inc. is assembled to allow continuous atmospheric distillation by feeding a mixture of an aqueous solution of 65 weight percent 3-chloro-2-hydroxypropyltrimethylammonium chloride (CHPTMAC) (commercially available from The Dow Chemical Company under the trade designation QUAT ™ 188) and 1,3-dichloro-2-propanol. The apparatus is used to distill overhead the water/1,3-dichloro-2-propanol minimum-boiling heterogeneous azeotrope. The overhead vapors are condensed and allowed to separate into 1,3-dichloro-2-propanol and aqueous phases in a reflux tank/phase separator, and the aqueous portion is returned to the column as reflux. Overhead temperatures measured above the top tray and are in the range of 92°–99° C. at atmospheric pressure. A liquid mixture containing 7.1 weight percent 1,3-dichloro-2-propanol (DCP) in the aqueous CHPTMAC is delivered into the twentieth tray of a 40-tray column and the measurements in Table 2 are made at the indicated times. Measurements on runs 13–15 are taken after some accummulated bottoms from runs 1–12 (containing 0.020% DCP) is used as feed on the twentieth tray.

The data obtained during the distillation runs are shown in Table 2:

TABLE 2

| Run | Time into run, min | Feed ml/min | Reflux ml/min | Over-head ml/min | Bottoms Temp °C. | Weight Percent DCP* in bottoms |
|---|---|---|---|---|---|---|
| | 7.1 weight percent DCP* Feed on 20th | | | | | |
| 1 | 160 | 5.0 | 1.8–2.0 | 0 | 112.5 | 4.66 |
| 2 | 242 | 2.5 | 4.75 | 0.15 | 115 | 0.70 |
| 3 | 95 | 2.5 | 5.5 | 0.15 | 124 | 0.052 |
| 4 | 160 | 2.5 | 5.0 | 0.20 | 115 | 0.012 |
| 5 | 210 | 2.5 | 5.0 | 0.40 | 115.5 | 0.013 |
| 6 | 250 | 2.5 | 5.0 | 0.28 | 116 | 0.021 |
| 7 | 305 | 2.5 | 5.0 | 0.30 | 117 | 0.018 |
| 8 | 350 | 2.5 | 5.0 | 0.30 | 117 | 0.017 |
| 9 | 160 | 2.5 | 4.75 | — | — | 0.022 |
| 10 | 250 | 2.5 | 4.75 | — | — | 0.016 |
| 11 | 305 | 2.5 | 4.75 | — | — | 0.019 |
| 12 | 340 | 2.5 | 4.75 | — | — | 0.016 |
| | 0.020 weight percent DCP* Feed on 20th | | | | | |
| 13 | 80 | 2.5 | 4.75 | 0 | 114 | 0.0002 |
| 14 | 250 | 2.5 | 4.75 | 0 | 116 | nd |
| 15 | 305 | 2.5 | 4.75 | 0 | 118 | nd |

*DCP is 1,3-dichloro-2-propanol
**"nd" means "not detectable" (less than 2 ppm).
A "—" is used when no measurement is taken because conditions are unchanged.

The data indicate that it is possible to remove 1,3-dichloro-2-propanol from crude CHPTMAC by azeotropic distillation; however, it requires a high boil-up rate (the amount of material vaporized within the column versus the amount feed to the column) of at least 200 percent (overhead liquid/feed liquid) and between about 40 to about 80 trays as determined by the fact that two passes are required in a 40-tray column to reduce DCP content to less than 2 ppm.

What is claimed is:

1. In a process for producing halohydroxypropyl-trialkylammonium halides by reacting, in a reaction mixture, a trialkylamine salt with an epihalohydrin, the improvement comprising using 1,3-dihalo-2-propanol as a cosolvent.

2. The process of claim 1 wherein the reaction mixture comprises 1,3-dihalo-2-propanol, water, epihalohydrin, and trialkylamine salt, and the 1,3-dichloro-2-propanol makes up at least about 10 weight percent of the reaction mixture.

3. The process of claim 2 wherein halogen atoms in the 1,3-halo-2-propanol, epihalohydrin, and trialkylamine salt are the same halogen.

4. The process of claim 3 wherein halohydroxypropyltrialkylammonium chloride product is produced which is substantially without diquaternary by-product.

5. The process of claim 3 wherein the halogen atoms are bromine.

6. The process of claim 3 wherein the halogen atoms are chlorine.

7. The process of claim 6 wherein the trialkyl amine salt is a trialkylamine hydrochloride.

8. The process of claim 7 wherein each alkyl group of the trialkyl amine hydrochloride independently has from about 1 to about 20 carbon atoms.

9. The process of claim 8 wherein the trialkyl amine is trimethylamine, dimethyl stearyl amine or dimethyl dodecylamine.

10. The process of claim 9 wherein 1,3-dichloro-2-propanol cosolvent is separated from the reaction mixture and recycled for use with additional trialkylamine hydrochloride and epichlorohydrin.

11. The process of claim 9 wherein the trialkylamine salt is trimethylamine hydrochloride.

12. The process of claim 2 wherein the 1,3-dihalo-2-propanol is separated from the reaction mixture and recycled for use with additional trialkylamine salt and epihalohydrin.

13. The process of claim 2 wherein each alkyl group of the trialkyl amine hydrochloride independently has from about 1 to about 20 carbon atoms.

14. The process of claim 13 wherein the process occurs at a temperature between 0° and 50° C.

* * * * *